| United States Patent [19] | [11] Patent Number: 4,628,124 |
| --- | --- |
| McKinnie et al. | [45] Date of Patent: Dec. 9, 1986 |

[54] TETRABROMOBISPHENOL-A PROCESS

[75] Inventors: Bonnie G. McKinnie, Baton Rouge, La.; Olan W. Mitchell, Magnolia, Ark.

[73] Assignee: Ethyl Corporation, Richmond, Va.

[21] Appl. No.: 778,710

[22] Filed: Sep. 23, 1985

[51] Int. Cl.$^4$ ............................................. C07C 39/16
[52] U.S. Cl. ..................................... 568/726; 568/779
[58] Field of Search ............................... 568/726, 779

[56] References Cited

U.S. PATENT DOCUMENTS

| | | | |
| --- | --- | --- | --- |
| 3,182,088 | 5/1965 | Hennis | 568/726 |
| 3,234,289 | 2/1966 | Hennis | 568/726 |
| 3,546,302 | 12/1970 | Asodorian et al. | 568/726 |
| 3,868,423 | 2/1975 | Montanari et al. | 568/726 |
| 3,929,907 | 12/1975 | Janzon et al. | 568/726 |
| 4,013,728 | 3/1977 | Brackenridge | 568/726 |
| 4,036,894 | 7/1977 | Jenker | 568/726 |
| 4,112,242 | 9/1978 | Swietoslwski et al. | 568/726 |

*Primary Examiner*—Werren B. Lone
*Attorney, Agent, or Firm*—Donald L. Johnson; John F. Sieberth; Joseph D. Odenweller

[57] ABSTRACT

Tetrabromobisphenol-A is made in high purity by adding a methanol-bromine solution to a methanol-bisphenol-A solution with vigorous agitation. Use of the bromine-methanol solution reduces the amount of by-products compared to use of liquid bromine feed.

9 Claims, No Drawings

TETRABROMOBISPHENOL-A PROCESS

BACKGROUND OF THE INVENTION

Tetrabromobisphenol-A is 4,4'-isopropylidenebis(2,6-dibromophenol). It is a widely used commercial fire retardant. There have been numerous publications on how it can be made. Hennis, U.S. Pat. No. 3,234,289, describes a process in which bisphenol-A (i.e. 4,4'-isopropylidenebisphenol) is placed in a water-alcohol mixture and liquid bromine is added at 22°–28° C. followed by reflux. Majewski et al., U.S. Pat. No. 3,363,007, discloses a process for brominating bisphenol-A in a mixture of water and an alkyl ether of a lower glycol.

Asadorian et al., U.S. Pat. No. 3,546,302, discloses a bromination process conducted in a two-phase solvent having an aqueous phase and an organic phase.

Montanari et al., U.S. Pat. No. 3,868,423, discloses the bromination of isopropylidenebisphenol with liquid bromine and gaseous chlorine in a methanol solvent. Janzon et al., U.S. Pat. No. 3,929,907, discloses the bromination of bisphehols in the presence of aqueous hydrogen peroxide.

Brackenridge, U.S. Pat. No. 4,013,728, teaches a process for brominating bisphenol-A in aqueous acetic acid followed by a heating step. Jenkner, U.S. Pat. No. 4,036,894, discloses bromination of bisphenol-A in acetic acid with recycle of the mother liquor and addition of alkaline or alkaline earth metal acetate.

Production of tetrabromobisphenol-A by dissolving bisphenol-A in methanol and adding liquid bromine is an effective way to make tetrabromobisphenol-A but the product contains various impurities which detract from its commercial value. These impurities include brominated phenols and hydrolyzable impurities. A need exists for a process that would lower the amount of these impurities.

SUMMARY OF THE INVENTION

It has now been discovered that the amount of impurities in tetrabromobisphenol-A can be sharply decreased by using a process in which bisphenol-A is dissolved in methanol and brominated by adding a solution of bromine in methanol to the bisphenol-A methanol solution. It has been shown that the amount of impurities can be sharply reduced from about 4 weight percent down to as little as 0.2 weight percent.

The amount of methanol used to dissolve the bisphenol-A can vary over a wide range. A useful range is about 1.0–6 parts by weight methanol per each part bisphenol-A. A more preferred range is about 1.5–3 parts by weight methanol per each part bisphenol-A and the most preferred amount is about 2.0 parts methanol per each part bisphenol-A.

The amount of bromine dissolved in the alcohol can vary widely. The more dilute the bromine solution, the better the results. However, excessive dilution causes an unacceptable drop in production per unit volume of reactor. A useful range in which to operate is about 1–4 parts by weight bromine per each part methanol. A more preferred range is about 1–3 parts bromine per each part methanol. The most preferred amount is about 2 parts bromine per each part methanol.

The amount of methanol-bromine solution added should be an amount that supplies sufficient bromine to make an acceptable product. The stoichiometric requirement is 4 moles of bromine per mole of bisphenol-A. A useful range in which to operate is about 3.9–4.5 moles of bromine per mole of bisphenol-A and the most preferred range is 4.0–4.1 moles bromine per mole of bisphenol-A.

The bromine-methanol solution should not be premixed much in advance of when it will be used because the bromine will react to some extent with the methanol. If pre-mixed, the solution should be kept cold, e.g. under 10° C., until it is used. In a preferred mode of operation the methanol and bromine are blended in-line just prior to introduction into the methanol-bisphenol-A solution.

Preferably the bromine-methanol solution is introduced below the liquid surface of the methanol-bisphenol-A solution and more preferably it is introduced in an area of high agitation. Other methods of diluting the bromine feed with methanol may be used. For example the bisphenol-A may be dissolved in all of the methanol to be used and brought to reflux. The bromine can then be added to the reflux return stream. This method is equivalent to the method of forming a bromine-methanol solution and adding the solution.

Rapid mixing of the bromine-methanol and bisphenol-A-methanol is highly preferred in order to obtain the best results with the new mode of bromine addition.

The bromine-methanol solution may be fed to the reaction mixture at an initial temperature that is ambient or lower although this is not essential. For example the bromine feed can be started at temperatures from −10° up to about 30° or somewhat higher, e.g. 0°–35° C. if that is what the liquid happens to be at. As the feed progresses the temperature will rise due to the heat of the reaction. Sometime during the feed the temperature will attain reflux conditions and reflux can be continued through the end of the feed of the bromine-methanol solution although reflux is not essential as long as the reaction is continued long enough to substantially complete the bromination. After this, heat can be applied to maintain reflux for a short period of time of say 10 minutes to 1 hour to assure completion of the reaction.

During the bromine-methanol feed, the bromination of bisphenol-A forms HBr which reacts with the methanol to form methyl bromide. The methyl bromide vaporizes and can be collected from the off-gas and marketed as a commercial product for its many known uses such as soil fumigation.

Tetrabromobisphenol-A can be recovered from the reaction mixture using conventional methods. For example the final reaction mixture can be diluted with water and filtered to recover the tetrabromobisphenol-A. The product can then be dried in an oven to remove water, methanol, bromine, HBr and other volatiles.

The following examples serve to illustrate how the process is carried out and to compare it to a prior art process using liquid bromine feed rather than feeding a bromine-methanol solution.

EXAMPLE 1

Comparative Example

In a reaction vessel fitted with a condenser, heating mantle, thermometer, stirrer and addition funnel with a dip tube was placed 223 grams of methanol (3% water) and 52.65 grams bisphenol-A. While stirring this was heated to reflux and 154.5 grams of bromine was added through the dip leg over a 80 minute period at reflux. Reflux was continued for 8 minutes and then $Na_2SO_3$ was added to destroy unreacted bromine. A small sample of the product was removed and dissolved in methylene chloride, washed with water and dried over anhydrous sodium sulfate. The methylene chloride was evaporated and N,o-bis(trimethylsilyl) trifluoroacetamide added to derivatize the product which was then analyzed by gas chromatography.

EXAMPLE 2

A reaction vessel was charged with 54.16 grams bisphenol-A and 122 grams methanol (3% water). A solution of 165 grams bromine in 85 grams methanol was prepared with cooling. While stirring at the same rate as in Example 1, the bromine-methanol solution was added slowly to the bisphenol-A solution starting at room temperature. When one-third of the bromine solution was added, the reaction mixture reached reflux. It was maintained at reflux through the remainder of the feed. Feed time was 84 minutes. Reflux was continued for 8 minutes. Sodium sulfite was added to destroy unreacted bromine. A sample of product was worked-up and derivatized as in Example 1 and analyzed by gas chromatography.

Analysis of the tetrabromobisphenol-A from Examples 1 and 2 is shown in the following table.

| Compound | Amount (area %) | |
|---|---|---|
| | Example 1 | Example 2 |
| TBBPA | 95.57 | 99.14 |
| Tribromobisphenol A | 0.05 | 0.277 |
| Dibromobisphenol A | ND[4] | 0.030 |
| Tribromophenol | 2.5 | 0.188 |
| Dibromophenol | ND | 0.068 |
| Bromophenol | ND | 0.014 |
| Compound A[1] | 0.83 | 0.078 |
| Compound B[2] | 0.22 | 0.036 |
| Compound C[3] | 0.58 | 0.118 |
| Unknown | ND | 0.009 |

[1] 1-bromo-2-(3,5-dibromo-4-hydroxyphenyl)-2-methoxypropane.
[2] 1,1-dibromo-2-(3,5-dibromo-4-hydroxyphenyl)-2-methoxypropane.
[3] 1,3-dibromo-2-(3,5-dibromo-4-hydroxyphenyl)-2-methoxypropane.
[4] ND means present but not determined.

The results show that the tetrabromobisphenol-A made in Example 2 by the present process is significantly higher in purity compared to Example 1 made by a prior art process.

The improved process is applicable to the bromination of other bisphenols. These are compounds of the structure

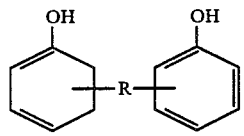

wherein R is a divalent aliphatic hydrocarbon group of 1-4 carbon atoms or a direct bond between the two benzene rings. Representative examples are 4,4'-methylenebisphenol, 2,2'-methylenebisphenol, 2,4'-methylenebisphenol, 4,4'-ethylidenebisphenol, 2,2'-ethylidenebisphenol, 2,4'-ethylidenebisphenol, 2,2'-isopropylidenebisphenol, 2,4'-isopropylidenebisphenol, 4,4'-butylidenebisphenol, 2,2'-butylidenebisphenol, 4,4'-biphenol, 2,2'-biphenol, 2,4'-biphenol and the like. These bisphenols can be substituted for the bisphenol-A, i.e. 4,4'-isopropylidenebisphenol, used in the foregoing description and examples of the present invention. All of the products can be used as fire retardants in a broad range of organic materials normally susceptible to combustion in the presence of air and an ignition source.

We claim
1. A process for brominating bisphenol-A to make mainly tetrabromobisphenol-A while minimizing the formation of by-products, said process comprising:
(a) dissolving bisphenol-A in methanol in a weight ratio of about 1-6 parts methanol per each part bisphenol-A,
(b) feeding a solution of bromine in methanol to the bisphenol-A solution with stirring the bromine:methanol weight ratio in said bromine solution being about 1-4:1, and
(c) recovering tetrabromobisphenol-A.
2. A process of claim 1 wherein said bromine solution is added at a reaction temperature initially at about 0°-35° C. and finally at reflux.
3. A process of claim 1 wherein said methanol:bisphenol-A weight ratio is about 1.5-3:1.
4. A process of claim 3 wherein said bromine:methanol weight ratio is about 1-3:1.
5. A process of claim 4 wherein said bromine solution is added in an amount to provide about 4 moles of bromine per mole of bisphenol-A
6. A process for brominating a bisphenol to make mainly tetrabromobisphenol while minimizing formation of by-products, said process comprising:
(a) dissolving said bisphenol in methanol in a weight ratio of about 1.5-3 parts methanol per each part bisphenol,
(b) feeding a solution of bromine in methanol to the bisphenol solution with stirring the bromine:methanol weight ratio in said bromine solution being about 1-4:1, and
(c) recovering a tetrabromobisphenol.
7. A process of claim 1 conducted in a temperature range of about −10° C. up to reflux.
8. A process of claim 6 conducted in a temperature range of about −10° C. up to reflux.
9. A process of claim 8 wherein the bromine-methanol feed is started in a temperature range of about −10° C. up to about 30° C. and the reaction mixture is refluxed to complete the bromination.

* * * * *